(12) United States Patent
Rathod et al.

(10) Patent No.: US 6,756,502 B2
(45) Date of Patent: Jun. 29, 2004

(54) INTERMEDIATE AND PROCESSES FOR ITS PREPARATION AND CONVERSION INTO A PHARMACOLOGICALLY-ACTIVE AGENT

(75) Inventors: Dhiraj Mohansinh Rathod, Vadodara (IN); Srinivasan Rengaraju, Vadodara (IN); Milind Moreshwar Gharpure, Vadodara (IN); Nishant Mahendra Patel, Vadodara (IN); Mandar Manohar Deoahar, Vadodara (IN)

(73) Assignee: Alembic Limited, Gujarat (IN)

( * ) Notice: Subject to any disclaimer, the term of this patent is extended or adjusted under 35 U.S.C. 154(b) by 57 days.

(21) Appl. No.: 10/119,287

(22) Filed: Apr. 10, 2002

(65) Prior Publication Data

US 2003/0195376 A1 Oct. 16, 2003

(30) Foreign Application Priority Data

Apr. 10, 2001 (EP) ............................. 01303347

(51) Int. Cl.$^7$ ................ C07D 303/46; C07D 301/02; C07C 211/17
(52) U.S. Cl. ............ 549/519; 549/512; 549/332; 564/336; 564/355; 564/358
(58) Field of Search ............... 549/519, 512, 549/332; 564/336, 355, 358

(56) References Cited

U.S. PATENT DOCUMENTS 4,535,186 A * 8/1985 Husbands et al. .......... 564/336

FOREIGN PATENT DOCUMENTS

| EP | 0 112 669 | 7/1984 |
| GB | 2 227 743 | 8/1990 |

OTHER PUBLICATIONS

Stork et al; J. Am. Chem. Soc., vol. 82, pp 4315–4323, 1960.*

Wong et al., J. Med. Chem., vol. 27, No. 1, pp 20–27, 1984*

Zhou, Jin Pei, et al., "Studies on Synthesis of Antidepressant Venlafaxine", *Journal of China Pharmaceutical University*, Apr. 30, 1999, pp. 249–250 (With English–language translation).

* cited by examiner

*Primary Examiner*—Ba K. Trinh

(57) ABSTRACT

Processes for the preparation of Venlafaxine (IX) via the novel epoxy-nitrile intermediate (I), which when subjected to hydrogenation forms compound (X), and may subsequently be reduced to yield the desired product (IX). The epoxy-nitrile intermediate (I) itself may be synthesized via various alternative reaction strategies, from a range of starting materials. E.g. 4-methoxy-benzaldehyde (VI), upon treatment with cyclohexyl magnesium bromide yields compound (V). This in turn may be oxidized to yield compound (III), which forms compound (II) on treatment with an (x-keto-halogenation agent. Cyanation of compound (II), then yields the desired epoxy nitrile intermediate (I), from which Venlafaxine (IX) may be synthesized.

31 Claims, 3 Drawing Sheets

Figure 1:
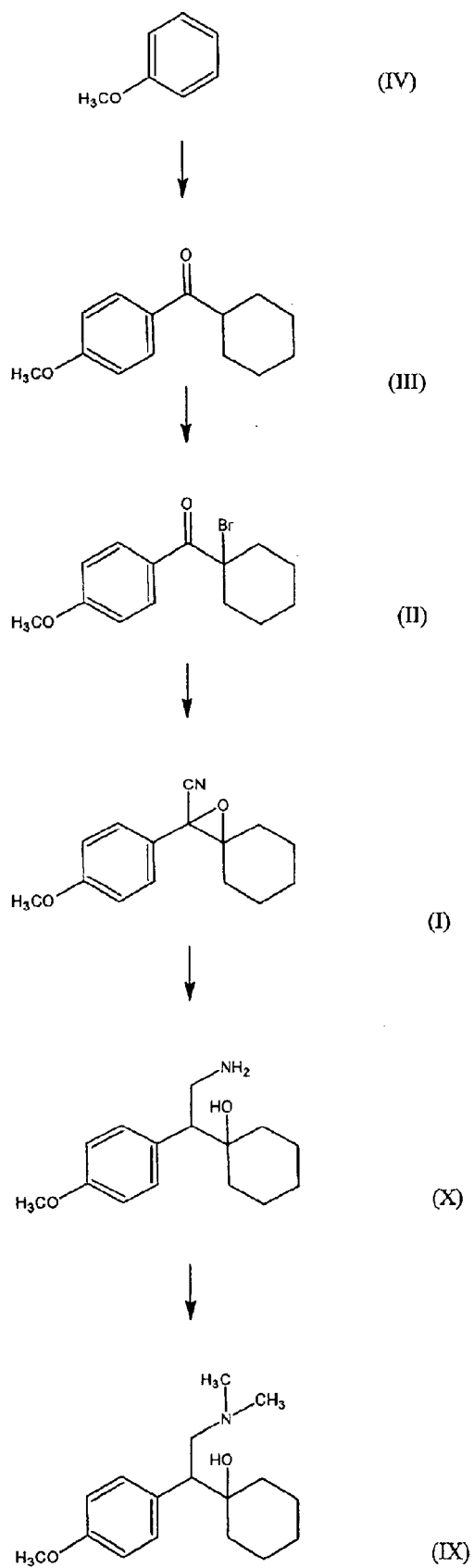

INTERMEDIATE AND PROCESSES FOR ITS PREPARATION AND CONVERSION INTO A PHARMACOLOGICALLY-ACTIVE AGENT

CROSS-REFERENCE TO RELATED APPLICATIONS

This application claims priority to European Patent Application No. 01303347.7-2117, filed Apr. 10, 2001, the contents being incorporated by reference herein.

BACKGROUND OF THE INVENTION

This invention relates to a novel intermediate which is valuable in the synthesis of a known medicament by a more advantageous route. The invention further relates to processes by which such an intermediate may first be itself prepared and thereafter may be converted into the known anti-depressant (±)-1-[2-dimethylamino-1-(4-methoxy-phenyl)-ethyl]-cyclohexanol of structural formula (IX):

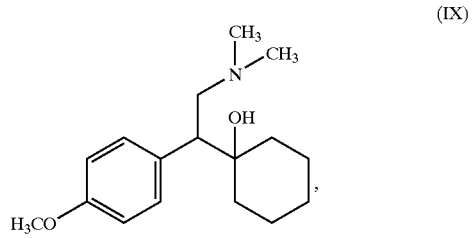

(IX)

and pharmacologically-acceptable salts thereof, e.g. Venlafaxine hydrochloride, supplied by American Home Products, Inc., under the trade name Effexor®.

Venlafaxine selectively inhibits the neuronal uptake of serotonin-norepinephrine and to a lesser extent dopamine. Studies indicate that it has comparable or possibly slightly greater efficacy to other selective serotonin reuptake inhibitors (SSRI's). It appears to be as effective as standard antidepressants such as imipramine. Venlafaxine's unique chemical structure and neuro-pharmacological activity give it a broader spectrum of activity than other antidepressants.

Previously known methods for the preparation of Venlafaxine include e.g. that taught in EP 0,112,669, which discloses the preparation of various 2-aryl-2-(1-hydroxycyclohexyl)ethylamine derivatives via α-aryl-α-(1-hydroxy-cyclohexyl) acetonitriles or α-aryl-N,N-dimethyl-α-(1-hydroxycyclohexyl) acetamide as chemical intermediates. These chemical intermediates are prepared by condensing α-arylacetonitriles or -aryl-N,N-dimethyl acetamides with cyclohexanone.

GB 2,227,743 discloses the preparation of 2-(1-hydroxycyclohexylethyl-thioacetamide) derivatives for the synthesis of Venlafaxine. The thioacetamido derivative is prepared from 4-methoxyacetophenone via Kindler modification of the Willgerodt reaction.

Zhou Jinpei et al. (Zhongguo Yaoke Daxue Xuebao (Journal of China) 1999, 30(4), 249–250) have reported the synthesis of Venlafaxine using methoxy-benzene as a starting material. The route involves 5 steps and gives 11% overall yield. In this route anisole is treated with chloroacetyl chloride under Friedel-Crafts acylation conditions followed by substitutions of α-halo-p-methoxyacetophenone by dimethylamine which is reduced by potassium borohydride to give a β-hydroxydimethylamine derivative. This intermediate, on treatment with $PBr_3$ followed by magnesium in tetrahydrofuran (THF), and subsequent treatment with cyclohexanone, yields Venlafaxine.

These known synthetic routes tend to involve the use of hazardous, costly and moisture sensitive reagents. For example, the synthesis described in EP 0,112,669 requires a very low reaction temperature (−50° C. to −70° C.), and a hydrogenation step which uses expensive rhodium catalyst. Materials in this route are not easily available, and the reaction conditions are harsh, with high demands on equipment, and high production costs.

The process taught in GB 2,227,743 uses a ratio of 50:1 Raney nickel to thioamide in its hydrogenation step, and also requires the use of toxic solvents such as dioxane for the reduction of thioamide. These reagents and conditions make this process commercially unattractive.

Zhou Jinpei's process requires the use of costly chemicals such as potassium borohydride and $PBr_3$, as well as the purification of an important intermediate via distillation under high vacuum, which further adds to the cost.

We have now evolved a synthetic route for the preparation of Venlafaxine which starts from easily available materials, and employs mild reaction conditions and simple after-treatment procedures, thus making it suitable for large-scale production. In this new route, hazardous, moisture-sensitive, and highly inflammable reagents are completely avoided, as are costly chemicals such as rhodium catalyst and potassium borohydride.

Certain alternatives are available in the early stages of this route, which is indeed advantageous since it opens the way to the use of different reaction strategies, from a range of starting materials, which may be selected according to cost and availability. All of these alternative routes however pass through the same novel epoxy nitrile intermediate.

According to the present invention, there is provided the epoxy-nitrile compound of structural formula (I):

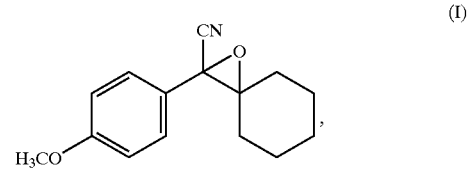

(I)

namely 2-(4-methoxy-phenyl)-1-oxa-spiro[2.5]octane-2-carbonitrile.

The present invention also provides a process for the preparation of the compound of formula (I), in which (1-bromo-cyclohexyl)-(4-methoxy-phenyl)-methanone of structural formula (II):

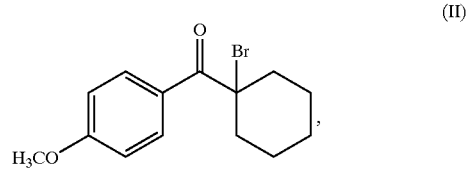

(II)

is subjected to treatment with a cyanation agent, so as to yield the epoxy nitrile intermediate of formula (I).

The cyanation agent employed is preferably sodium cyanide or potassium cyanide, although other cyanation agents may be used, such as trimethyl silyl cyanide, cuprous cyanide, other alkali and alkaline earth metal cyanides, or other cyanating agents known from the literature.

The reaction can be readily performed in solution in methanol at room temperature. Alternatively, solvents such as ethanol, isopropyl alcohol, acetonitrile, dimethyl formamide, dimethyl sulphoxide, dimethyl acetamide, hexamethylene phosphoric triamide (HMPT), ethyl acetate, or sulfolane, may be used, as may benzene, toluene, cyclohexane, dichloromethane, or chloroform, in the presence of a phase transfer catalyst. The phase transfer catalyst is required when using these non-polar solvents, as the solubility of inorganic cyanides therein is practically nil. The catalyst therefore acts so as to carry the cyanide ion to the organic phase for reaction.

The reaction may be carried out at a temperature in the range of from −10° C. to 60° C. Preferably the reaction temperature is in the range of from 20° C. to 25° C.

The reaction time may be in the range of from 2 to 48 hours, or more preferably is in the range of from 6 to 8 hours.

The ratio of solvent to (1-bromo-cyclohexyl)-(4-methoxyphenyl)-methanone (II) may be in the range of from 1:1 to 100:1. Preferably the ratio used is substantially 25:1.

Preferably, the process additionally comprises a further step of previously preparing the compound of formula (II), by subjecting cyclohexyl-(4-methoxy-phenyl)-methanone of structural formula (III):

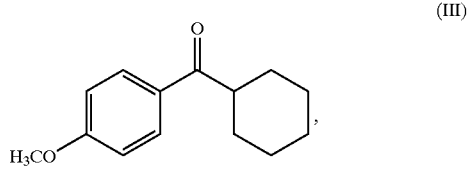

(III)

to treatment with an α-keto-halogenating agent, so as to give the compound of formula (II). A reaction for the preparation of the bromo-ketone (II) is reported in Bull. Soc. Chim. France (1962) 90–6.

The α-keto-halogenation is preferably effected using phenyltrimethyl ammonium perbromide. Alternatively, a brominating agent may be selected from liquid bromine, N-bromo succinimide, 1,3-dibromo-5,5-dimethylhydantoin, quaternary ammonium and phosphonium perbromides, N-chlorosuccinimide, and other halogenating agents known in the literature.

The solvent used may be selected from methanol, acetic acid, benzene, toluene, chloroform, carbon tetrachloride, tetrahydrofuran (THF), acetonitrile, ethanol, dichloromethane, dioxane, t-butanol, and substituted benzenes.

The reaction is preferably carried out at a temperature of substantially 68° C., for a time of about 6 hours.

The ratio of solvent to ketone may be in the range of from 1:1 to 100:1, but preferably is substantially 20:1.

At this point it should be noted that the starting point for the above-described stage in the overall syntheses, namely cyclohexyl-(4-methoxy-phenyl)-methanone of formula (III), is itself a known compound, disclosed in Izv.Akad.Nauk Turkm.SSR.Ser.Fiz-Tekhn.,Khim.iGeol.Nauk 1963, No. 1,115-6. The overall process of the present invention therefore may include an additional step of subjecting methoxy-benzene of structural formula (IV):

(IV)

to Friedel-Crafts acylation treatment so as to yield the compound of formula (III).

Thus, the cyclohexyl-(4-methoxy-phenyl)-methanone (III) may for instance be synthesized by Friedel-Crafts reaction between cyclohexane-carbonyl chloride and methoxy-benzene in the present of aluminium trichloride:

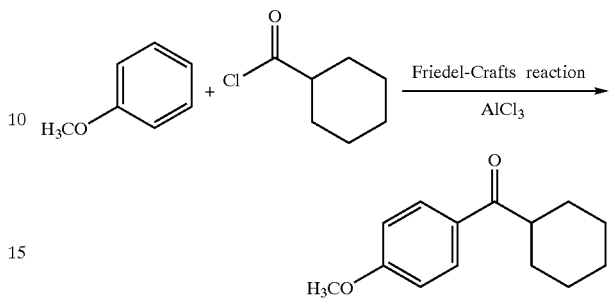

Alternatively, boron trifluoride or sodium aluminium chloride may also be used as the Friedel-Crafts reagent, in place of aluminium trichloride.

The solvent is selected from methoxy-benzene and halogenated or nitrated benzenes, and may be used in a ratio relative to the cyclohexane-carbonyl chloride in the range of from 5:1 to 50:1.

The reaction temperature may be in the range of from −20° C. to 40° C.

However, unless there are other, external reasons that argue for the use of methoxy-benzene as the primary starting material for the overall syntheses, we currently believe that the intermediate cyclohexyl-(4-methoxy-phenyl)-methanone (III) may usually be better produced in an alternative manner.

It is thus preferred that the previously-outlined process of this invention should instead further comprise an additional step of subjecting cyclohexyl-(4-methoxy-phenyl)-methanol of structural formula (V):

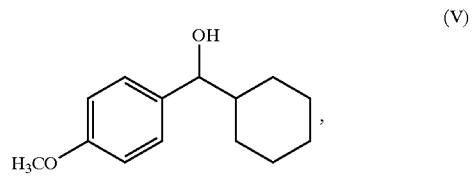

(V)

to oxidation so as to yield the cyclohexyl-(4-methoxy-phenyl)-methanone (III).

Oxidation is preferably performed using chromic acid, which may desirably be formed in situ by the reaction of sodium dichromate dihydrate with sulphuric acid. Alternatively, an oxidising agent may be selected from alkali and alkaline earth metal chromates and dichromates, chromic anhydride, manganese dioxide, alkali and alkaline earth metal manganates, permanganates, nitric acid, alkali and alkaline earth metal persulphates, quaternary ammonium and phosphonium manganates and permanganates, chromates and other oxidising agents known in the literature.

The oxidation is preferably carried out at a temperature in the range of from 25° C. to 30° C., for a time of substantially 3 hours.

This alternative process preferably further comprises the initial step of subjecting 4-methoxy-benzaldehyde of structural formula (VI):

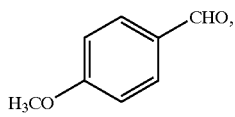 (VI)

to treatment with a cyclohexyl magnesium halide, $C_6H_{11}$—Mg—X (where X=chlorine, bromine or iodine) so as to yield cyclohexyl-(4-methoxy-phenyl)-methanol (V). The reaction is preferably carried out using cyclohexyl magnesium bromide in THF at a temperature in the range of from 10° C. to 15° C. for a period of substantially one hour. The cyclohexyl magnesium bromide may desirably be formed in situ by the reaction of cyclohexyl bromide with magnesium turnings.

Alternatively, the 4-methoxy-benzaldehyde (VI) may be treated with an organometallic reagent such as cyclohexyl lithium or dialkylcupro lithium. Besides THF, the solvent used may also be selected from diethyl ether, dibutyl ether, dipropyl ether, di-isoproyl ether, dioxane, diglyme, or alkylated polyethers.

An alternative preparation of cyclohexyl-(4-methoxyphenyl)-methanol (V) may be performed by treating the compound of formula (XI):

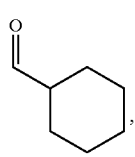 (XI)

namely cyclohexanecarbaldehyde, with anisyl magnesium halide or anisyl lithium.

In a quite different alternative process according to the present invention, the compound corresponding to formula (VII):

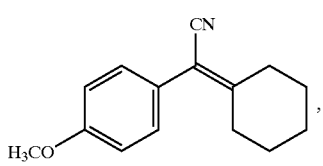 (VII)

namely cyclohexylidene-(4-methoxy-phenyl)-acetonitrile, is treated with an epoxidating agent, such as m-chloroperbenzoic acid (m-CPBA) to yield the desired compound of formula (I).

The epoxidating agent may alternatively be selected from perbenzoic acid, peracetic acid, performic acid and other organic peracids, hydrogen peroxide, persulphuric acid, alkylhydroperoxides, and other epoxidating agents known in the literature.

The solvent for the epoxidation is selected from dichloromethane, dichloroethane, carbon tetrachloride, chloroform, ethyl acetate and toluene. Preferably, the solvent used is dichloromethane.

The reaction temperature may be in the range of from 0° C. to the reflux temperature of the corresponding solvent but will preferably be substantially 40° C. The reaction time may be in the range of from 1 hour to 48 hours, but will preferably be in the range of from 6 to 8 hours.

Preferably, the second alternative process further comprises a previous step of preparing the compound of formula (VII), by treating the compound corresponding to formula (VIII):

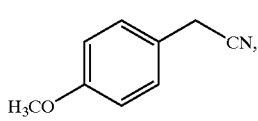 (VIII)

namely (4-methoxy-phenyl)-acetonitrile, with cyclohexanone and a condensing agent such as sodium methoxide, to secure the compound of formula (VII). This reaction is reported in U.S. Pat. No. 2,647,122.

The condensing agent may alternatively be selected from sodium ethoxide, potassium t-butoxide, quaternary ammonium hydroxide and other alkali and alkaline earth metal alkoxides, alkali and alkaline earth metal hydrides, alkali and alkaline earth metal amides.

The solvent may be selected from methanol, ethanol, t-butanol and other solvents known to the art. Preferably methanol is used.

The reaction time may be in the range of from 1 to 24 hours, but preferably is in the range of from 3 to 6 hours.

The reaction temperature may be in the range of from 10° C. to 60° C., but is preferably room temperature, that is to say substantially 25° C.

A further possible alternative process for the preparation of 2-(4-methoxy-phenyl)-1-oxa-spiro[2.5]octane-2-carbonitrile (I), comprises subjecting the compound corresponding to formula (XII):

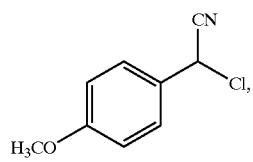 (XII)

namely chloro-(4-methoxy-phenyl)-acetonitrile, to Darzen's condensation (i.e. halohydrin formation, followed by cyclization), using cyclohexanone in the presence of a base.

The compound of formula (I), when thus prepared by any of the alternative processes as described above, may desirably be used as an intermediate in the preparation of the compound corresponding to formula (IX):

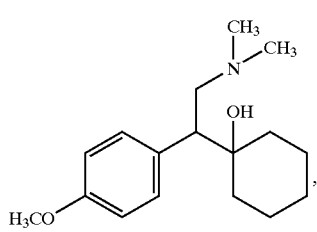 (IX)

namely (±)-1-[2-dimethylamino-1-(4-methoxy-phenyl)-ethyl]-cyclohexanol.

According to a further aspect of the present invention there is therefore provided a process for the preparation of the compound of structural formula (IX), which comprises the steps of:

(a) hydrogenating the epoxy-nitrile of structural formula (I) in the presence of a catalyst, so as to yield 1-[2-amino-1-(4-methoxy-phenyl)-ethyl]-cyclohexanol corresponding to formula (X):

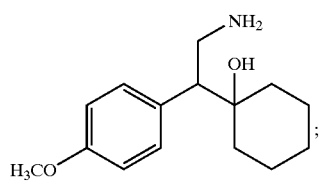

and (b) treating the 1-[2-amino-1-(4-methoxy-phenyl)-ethyl]-cyclohexanol (X) produced by step (a) above with formaldehyde and formic acid, in the presence of water; to yield the desired (±)-1-[2-dimethylamino-1-(4-methoxy-phenyl)-ethyl]-cyclohexanol.

The hydrogenation is preferably effected in the presence of Raney nickel catalyst, at a pressure in the range of from 500 to 1000 kPa. The ratio of Raney nickel to epoxy nitrile (I) may be in the range of from 5:1 to 1:5 by weight. Preferably, the ratio used is substantially 1:1.

Alternatively, the hydrogenation may be carried out using a reagent selected from platinum dioxide, platinum and palladium and nickel on different inert supports, aluminium hydride, lithium aluminium hydride, sodium borohydride, potassium borohydride, lithium borohydride in the presence of Lewis acids, or quaternary ammonium borohydrides, neat or in the presence of a phase transfer catalyst.

The hydrogenation reaction may be carried out at a temperature in the range of from 0° C. to 100° C., but is preferably carried out at room temperature.

The solvent may be selected from tetrahydrofuran (THF), dioxane, glyme, dialkylethers, polyethers and ethyl acetate.

Alternatively, the epoxynitrile (I) can be reduced to the desired amino compound (X) by treating it with ammonium formate and hydrogen, in the presence of a catalyst selected from noble metal or supported noble metal catalysts.

The treatment of compound (X) with formaldehyde and formic acid in step (b) is best performed at a temperature of substantially 100° C. for a time of substantially 6 hours, so as to yield 1-[2-dimethylamino-1-(4-methoxy-phenyl)-ethyl]-cyclohexanol of formula (IX), or Venlafaxine.

Alternatively, the epoxynitrile of structural formula (I) may be reduced to a hydroxynitrile intermediate of structural formula (XIII):

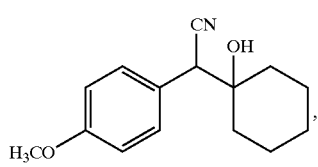

namely (1-hydroxy-cyclohexyl)-(4-methoxy-phenyl)-acetonitrile, using ammonium formate and a noble metal or supported noble metal catalyst. This hydroxynitrile compound (XIII) is then further reduced to the corresponding amino compound of formula (X) by treatment with Raney nickel, platinum dioxide, palladium, cobalt boride, nickel boride, or other suitable catalysts known from the literature.

Figure 2:
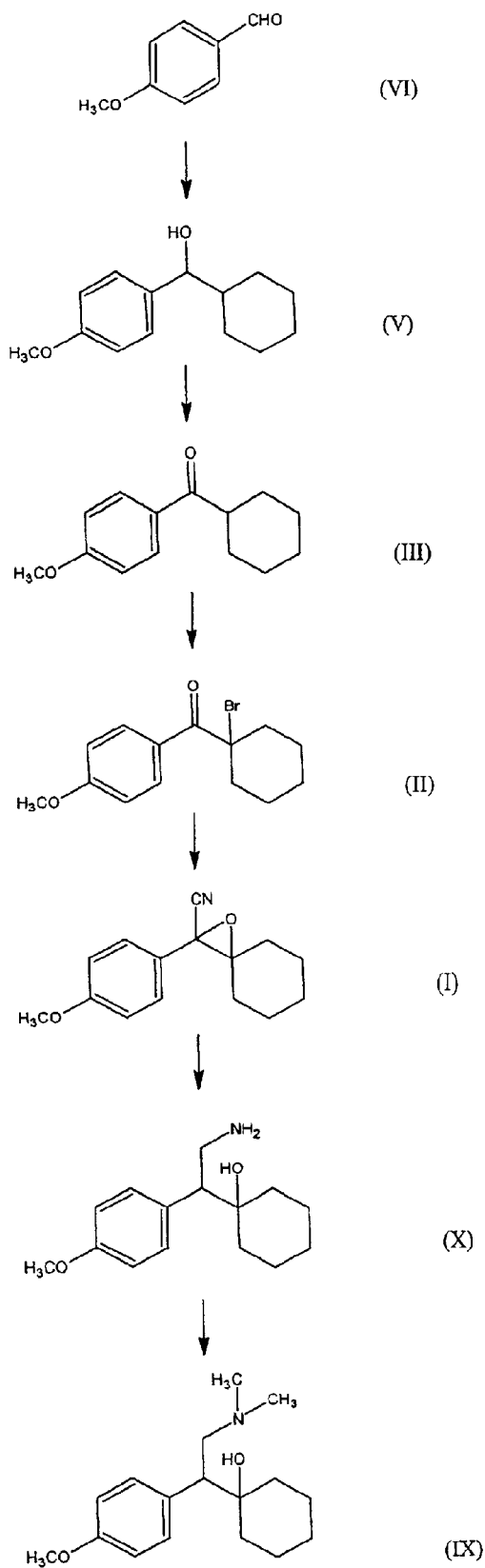
Figure 3:
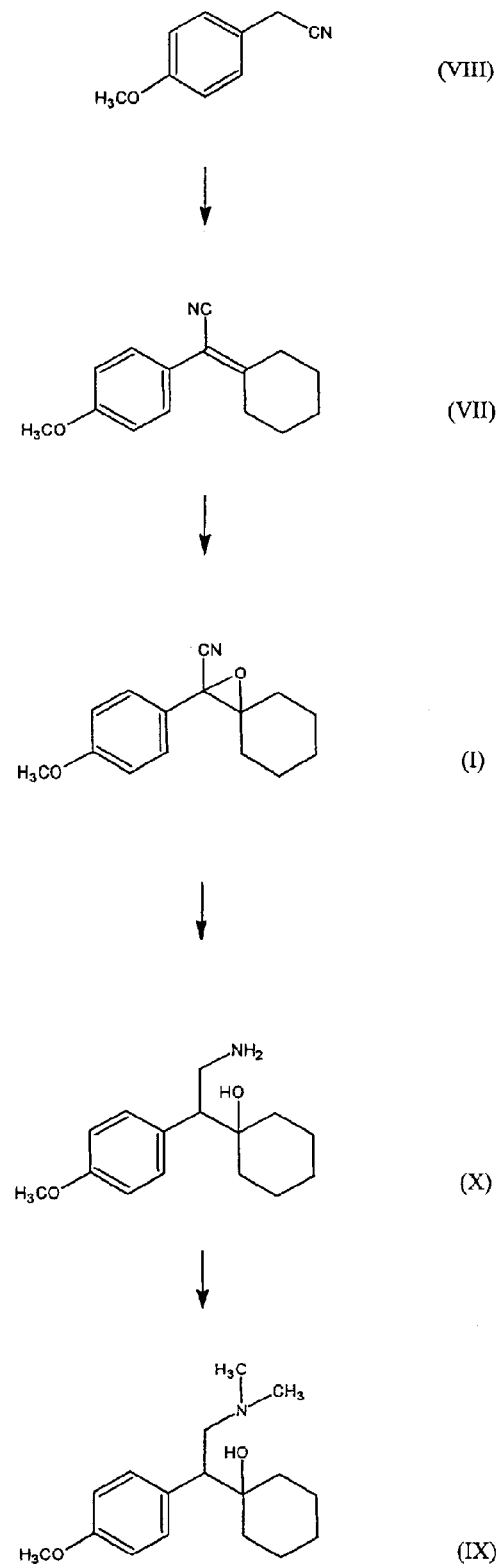

In order that the invention shall be well understood it will now be further described, but only for purposes of illustration with reference to the accompanying drawings, in which:

FIG. 1 is a reaction diagram showing the synthesis of (±)-1-[2-dimethylamino-1-(4-methoxy-phenyl)-ethyl]-cyclohexanol, Venlafaxine, via 2-(4-methoxy-phenyl)-1-oxa-spiro-[2.5]octane-2-carbonitrile of structural formula (I), from methoxy-benzene;

FIG. 2 is a reaction diagram showing the synthesis of (±)-1-[2-dimethylamino-1-(4-methoxy-phenyl)-ethyl]-cyclohexanol, Venlafaxine, via 2-(4-methoxy-phenyl)-1-oxa-spiro[2.5]octane-2-carbonitrile of structural formula (I), from 4-methoxy-benzaldehyde; and FIG. 3 is a reaction diagram showing the synthesis of (±)-1-[2-dimethyl-amino-1-(4-methoxy-phenyl)-ethyl]-cyclohexanol, Venlafaxine, via 2-(4-methoxy-phenyl)-1-oxa-spiro[2.5]octane-2-carbonitrile of structural formula (I), from (4-methoxy-phenyl)-acetonitrile.

Referring first to FIG. 1, it will be seen that this synthesis starts from methoxy-benzene of structural formula (IV), which is a readily-available starting material.

This is subjected to Friedel-Crafts acylation, to yield cyclohexyl-(4-methoxy-phenyl)-methanone of structural formula (III).

That in turn is subjected to a-keto-halogenation with a bromination reagent, to yield the corresponding (1-bromo-cyclohexyl)-(4-methoxy-phenyl)-methanone of structural formula The resultant product is then subjected to cyanation, yielding the desired intermediate 2-(4-methoxy-phenyl)-1-oxa-spiro[2.5]octane-2-carbo-nitrile (I).

Referring now to FIG. 2, this alternative synthesis starts from 4-methoxy-benzaldehyde (VI) which is subjected to treatment with cyclohexyl magnesium bromide to yield cyclohexyl-(4-methoxy-phenyl)-methanol (V). This in turn is then oxidised so as to yield cyclohexyl-(4-methoxy-phenyl)-methanone (III).

The subsequent reaction steps for the conversion of this compound to the desired intermediate, 2-(4-methoxy-phenyl)-1-oxa-spiro[2.5]octane-2-carbonitrile (I), are the same as those described above with reference to FIG. 1 for the corresponding conversion.

Referring now to FIG. 3, it will be seen that this further alternative synthetic route starts from (4-methoxy-phenyl)-acetonitrile (VIII), which is treated with a condensing agent, such as sodium methoxide, so as to yield cyclohexylidene-(4-methoxy-phenyl)-acetonitrile (VII). This in turn is then treated with an epoxidating agent, such as m-CPBA, so as to yield the desired intermediate, 2-(4-methoxy-phenyl)-1-oxa-spiro[2.5]octane-2-carbonitrile (I).

Having obtained the desired intermediate, 2-(4-methoxy-phenyl)-1-oxa-spiro[2.5]octane-2-carbonitrile (I), by any of the synthetic routes described above with reference to FIGS. 1 to 3, it is then hydrogenated in the presence of Raney nickel so as to yield 1-[2-amino-1-(4-methoxy-phenyl)-ethyl]-cyclohexanol (X). This in turn is then treated with formaldehyde and formic acid, in the presence of water, to yield (±)-1-[2-dimethylamino-1-(4-methoxy-phenyl)-ethyl]-cyclohexanol (IX).

In order that the invention shall be still better understood it will now be described in more detail, though only by way of illustration, with reference to the following Examples.

EXAMPLE 1

Preparation of 2-(4-methoxy-phenyl)-1-oxaspiro[2.5]octane-2-carbonitrile (I) from 4-methoxy-benzaldehyde (VI)

Stage 1: Preparation of cyclohexyl-(4-methoxy-phenyl)-methanol (V)

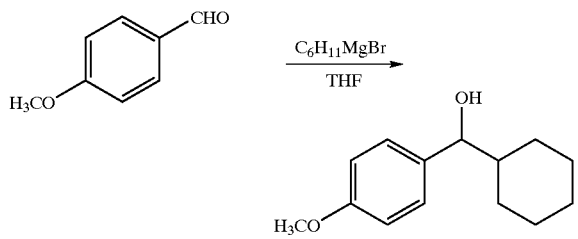

A reaction vessel was charged with 1.6 g Mg turnings in 50.0 ml tetrahydrofuran (THF). Cyclohexyl bromide was added thereto in small increments to initiate a reaction generating cyclohexyl magnesium bromide in situ, and thereafter the balance of 9.0 g thereof was added at reflux temperature. After completion of the addition, reflux was continued for 1 hour, and then the reaction mixture was cooled to 5 to 10° C. 5.0 g 4-methoxy-benzaldehyde was then slowly added while still maintaining the temperature between 5 and 15° C. The reaction mixture was allowed to warm up to 25° C., and stirred at that temperature for 6 hours. The mixture was dumped into a solution of 5.0 g ammonium chloride, and the organic layer was separated therefrom. The aqueous layer was extracted twice, each time with 25 ml ethyl acetate, and these extracts were combined with the organic layer and washed with brine solution. They were then dried over sodium sulphate, and the solvent was distilled off under vacuum.

6.5 g (dry product) of the desired cyclohexyl-(4-methoxy-phenyl)-methanol was thus obtained. After purification by column chromatography, eluting with Benzene:Ethyl acetate (90:10), it has the following characteristics:

| | |
|---|---|
| M.P: | 87 to 89° C. |
| NMR: | $^1$H NMR (CDCl$_3$) δ 7.2, 6.86 (q, 4H), δ 4.28 (d, 1H), δ 3.79 (s, 3H), δ 1.98 (d, 1H), δ 1.35 (m, 10H) |
| IR: | (cm$^{-1}$) 3630, 3459, 2942, 2855, 2623, 2527, 2446, 1253, 1034, 822. |
| Optical rotation: | Racemic |
| Solubility: | Soluble in methanol, ethanol, chloroform, dichloromethane, acetone, ethyl acetate etc. |

The same preparation has been carried out using cyclohexyl chloride or cyclohexyl iodide, and using THF as the solvent.

Stage 2: Preparation of cyclohexyl-(4-methoxy-phenyl)-methanone (III)

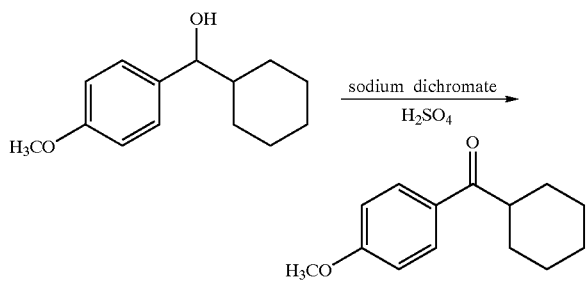

5 g of the product from Stage 1 and 5 ml water were charged into a reaction vessel. Separately a solution of chromic acid was prepared by dissolving 7.1 g sodium dichromate dihydrate in demineralized water, adding conc. sulphuric acid and cooling to room temperature. This chromic acid solution was then added to the reaction mixture while maintaining the temperature between 20 to 30° C., and then stirred therewith for 3 hours at room temperature. The mixture was extracted first with 15 ml and thereafter twice more with 5 ml each time of dichloromethane, and the combined dichloromethane layers were washed three times, each with 25 ml demineralized water. Then the organic layer was dried over sodium sulphate, and distilled to dryness under vacuum.

3.75 g of the desired cyclohexyl-(4-methoxy-phenyl)-methanone was thus obtained. After purification by column chromatography, eluting with Benzene:Ethyl acetate (80:20) it has the following characteristics:

| | |
|---|---|
| M.P: | 61 to 63° C. |
| NMR: | $^1$H NMR (CDCl$_3$) δ 7.93, 6.93 (q, 4H), δ 3.86 (s, 3H), δ 1.47 (m, 11H) |
| IR: | (cm$^{-1}$) 2926, 2855, 1660, 1602, 1509, 1260, 1176, 834. |
| Solubility: | Soluble in Methanol, ethanol, chloroform, dichloromethane, acetone, ethyl acetate, benzene, toluene and isopropyl alcohol. |

Stage 3: Preparation of (1-bromo-cyclohexyl)-(4-methoxy-phenyl)-methanone (II)

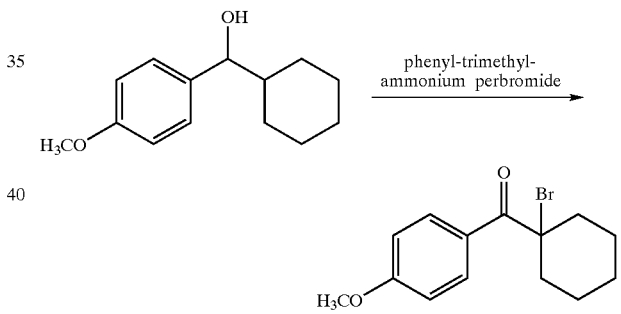

5 g of the product from Stage 2 was charged at room temperature into a reaction vessel with 50 ml THF and 8.56 g phenyl-trimethyl-ammonium perbromide and the resultant reaction mixture was refluxed for 2–3 hours. The reaction mixture was then dumped into water, and the resultant precipitate was filtered and washed with water.

The desired (1-bromo-cyclohexyl)-(4-methoxy-phenyl)-methanone was thus obtained, dry weight 5.6 g. After purification by column chromatography, eluting with Hexane:Benzene (30:40), it has the following characteristics:

| | |
|---|---|
| M.P: | 55 to 57° C. |
| NMR: | $^1$H NMR (CDl$_3$) δ 8.14, 6.9 (q, 4H), δ 3.86 (s, 3H), δ 1.57 (m, 10H) |
| IR: | (cm$^{-1}$) 2934, 2855.9, 1659.9, 1596.8, 1508, 1443, 1251, 1173, 846 |
| Solubility: | Soluble in methanol, ethanol, chloroform, dichloromethane, acetone, ethyl acetate, benzene, toluene and isopropyl alcohol. |

Stage 4: Preparation of 2-(4-methoxy-phenyl)-1-oxa-spiro [2.5] octane-2-carbonitrile (I)

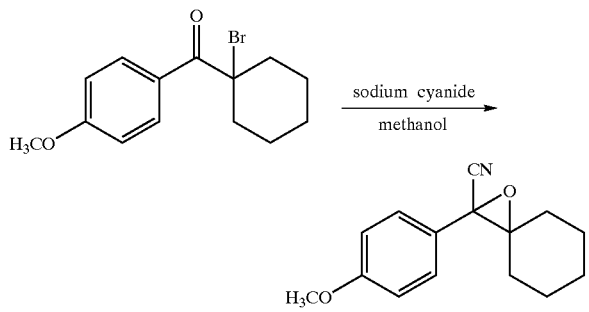

1 g of sodium cyanide was dissolved in 25 ml methanol at room temperature. 5 g of the product of Stage 3 was added thereto, and stirred at 25° C. for 2 hours. The reaction mixture was then dumped into 100 ml water and extracted first with 15 ml and thereafter twice more each time with 5 ml dichloromethane. The organic layers were separated, and washed three times, each with 25 ml demineralized water, and thereafter dried over sodium sulphate and distilled under vacuum.

The desired 2-(4-methoxy-phenyl)-1-oxa-spiro[2.5] octane-2-carbonitrile-was thus obtained, in a yield of 3.9 g of a viscous oil. After purification by column chromatography, eluting with Hexane:Benzene (30:40), it has the following characteristics:

| | |
|---|---|
| NMR: | $^1$H NMR (CDCl$_3$), δ 7.3, 6.85 (q, 4H), δ 3.75 (s, 3H), δ 1.52 (m, 10 H). |
| IR: | (cm$^{-1}$) 2935, 2856, 2238, 1611, 1514, 1448, 1252, 1174, 1034. |
| Optical rotation: | Racemic |
| Solubility: | Soluble in methanol, ethanol, chloroform, dichloromethane, acetone, ethyl acetate, benzene, toluene and isopropyl alcohol. |

The same reaction has also been successfully performed using potassium cyanide, in methanol at room temperature.

EXAMPLE 2

Preparation of 2-(4-methoxy-phenyl)-1-oxaspiro[2.5] octane-2-carbonitrile (I) by an alternative route from methoxy-benzene (IV)

Stage 1: Preparation of cyclohexyl-(4-methoxy-phenyl)-methanone (III) from methoxy-benzene (IV)

The same product as in Example 1, Stage 2 can also be synthesized by Friedel-Crafts reaction between cyclohexanecarbonyl chloride and methoxy-benzene as reported in the following journal:

Izv.Akad.Nauk Turkm.SSR.Ser.Fiz-Tekhn.,Khim.i Geol-.Nauk 1963, No.1,115-6

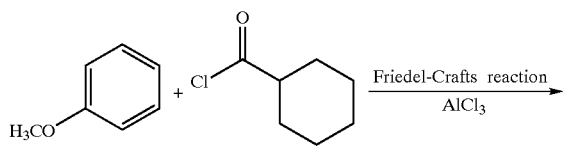

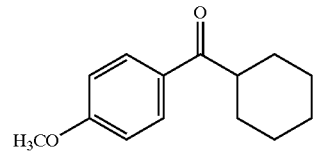

EXAMPLE 3

Preparation of 2-(4-methoxy-phenyl)-1-oxa-spiro[2.5] octane-2-carbonitrile (I) via an Alternative Route from (4-methoxy-phenyl)-acetonitrile (VIII)

Stage 1: Preparation of cyclohexylidene-(4-methoxy-phenyl)-acetonitrile (VII)

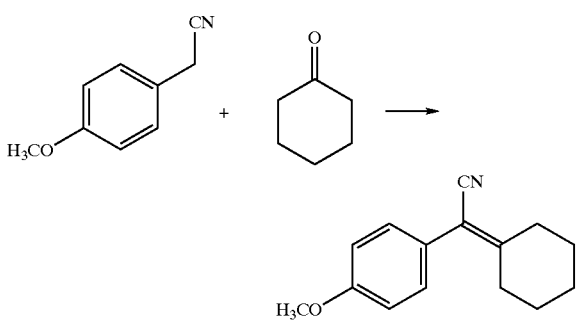

The reaction was carried out in methanol, using sodium methoxide or t-butanol and potassium t-butoxide at room temperature, and a reaction time of about 6 hours.

Stage 2: Preparation of 2-(4-methoxy-phenyl)-1-oxa-spiro [2.5]octane-2-carbonitrile (I)

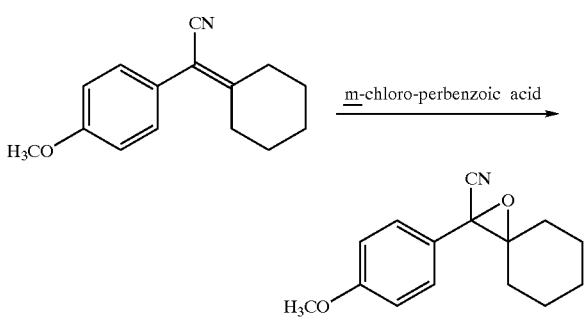

2.0 g of the product from Stage 1 was refluxed for 8 hours with 2.0 g of m-chloro-perbenzoic acid, in dichloromethane. The reaction mixture was cooled to room temperature and filtered to remove precipitated m-chloro-perbenzoic acid. The filtrate was washed with saturated sodium bicarbonate solution, and the dichloromethane layer was then dried over sodium sulphate. The solvent was distilled under reduced pressure, and the residue purified by column chloromatography using a hexane:benzene (8:2) mixture as the mobile phase.

The epoxidation has been carried out in various other solvents, namely chloroform, dichloroethane, acetonitrile and carbon tetrachloride, and at temperatures ranging from room temperature to reflux temperature.

EXAMPLE 4

Preparation of (±)-1-[2-dimethylamino-1-(4-methoxy-phenyl)-ethyl]-cyclohexanol (IX)

Stage 1: Preparation of 1-[2-amino-1-(4-methoxy-phenyl)-ethyl]-cyclohexanol (X)

5 g of the product obtained from Example 1 was added to a pressure vessel previously charged with 1 g of Raney Nickel suspended in ammoniacal ethanol, and the mixture was hydrogenated at 500 kPa pressure for 7 hours at room temperature. After checking completion of the reaction by TLC, the catalyst was filtered off through a hyflo bed, and ethanol was completely distilled off. The residue was taken up in isopropanolic HCl, cooled and the resultant solid filtered off. Demineralized water was added to the filtrate, and then extracted 3 times with 15 ml dichloromethane. The aqueous layer was rendered basic with caustic lye, extracted with ethyl acetate, and the ethyl acetate then distilled off under vacuum. Dry HCl gas was passed into the solution under cooling, yielding a solid precipitate, which was triturated in ether and filtered, yielding 4 g of the desired solid product, having the following characteristics:

| | |
|---|---|
| M.P: | 168 to 172° C. |
| NMR: | $^1$H NMR (DMSO d$_6$) δ 7.85 (s, 3H), δ 3.75 (s, 3H), δ 3.12 (m, 3H), δ 1.35 (m, 10H) |
| IR: | (cm$^{-1}$) 3403, 2930, 2850, 1609, 1511, 1245 |
| Optical rotation: | Racemic |
| Solubility: | Soluble in methanol, chloroform and water |
| Mass Spectra: | m/e = 250 |

This reduction has also been carried out using Raney nickel suspended in various solvents, e.g. methanol and ethanol, at room temperature and at a pressure in the range of from 500 to 1000 kPa.

Stage 2: Preparation of (±)-1-[2-dimethylamino-1-(4-methoxy-phenyl)-ethyl]-cyclohexanol (IX)

12 g of the product from Stage 1 above was added to a vessel containing 12.5 ml of 33% aqueous formaldehyde and 16.5 ml of 88% formic acid in 115 ml water, and the reaction mixture was heated to reflux for 6 hours. The solvent was then distilled off, and water was added to the residue and adjusted to pH 2 with conc. hydrochloric acid, and extracted with 100 ml ethyl acetate. The aqueous layer was rendered basic with 50% sodium hydroxide, and again extracted with ethyl acetate. The extract was washed with brine, dried, filtered and evaporated to a dry residue. This residue was dissolved in ethyl acetate, and treated with isopropanolic HCl, filtered and washed with chilled isopropyl alcohol.

10.0 g of the desired product were thus obtained, having the following characteristics:

| | |
|---|---|
| M.P: | 215 to 217° C. |
| NMR: | $^1$H NMR, δ 7.32, 6.98 (q, 4H), δ 3.78 (s, 3H, ), 3.64 (m, 2H), 3.06 (m, 1H), 2.74 (s, 6H), 1.38 (broad m, 10H) |
| Optical rotation: | Racemic |
| Solubility: | Soluble in methanol, chloroform and water |

The same reaction has also been carried out for periods of up to 12 hours.

The Applicants claim as their invention the new substances, processes and products therefrom as broadly defined in the appended claims, but they reserve their right also to claim preferred features as indicated below.

What is claimed is:

1. A compound corresponding to formula (I):

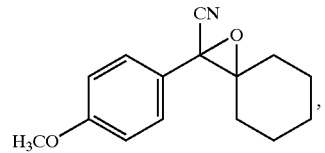

(I)

namely 2-(4-methoxy-phenyl)-1-oxa-spiro[2.5]octane-2-carbonitrile.

2. A process for the preparation of the compound of formula (I) as claimed in claim 1, in which the compound corresponding to formula (II):

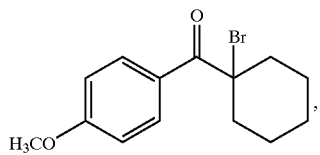

(II)

namely (1-bromo-cyclohexyl)-(4-methoxy-phenyl)-methanone, is subjected to treatment with a cyanation agent.

3. A process for the preparation of the compound of formula (I), as claimed in claim 2, which comprises a further step of previously preparing the compound of formula (II), by subjecting the compound corresponding to formula (III):

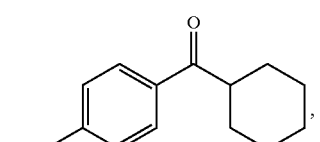

(III)

namely cyclohexyl-(4-methoxy-phenyl)-methanone, to treatment with an α-keto-halogenating agent.

4. A process for the preparation of the compound of formula (I), as claimed in claim 3, which further comprises an additional step of subjecting the compound of formula (IV):

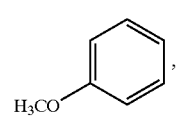

(IV)

namely methoxy-benzene, to Friedel-Crafts acylation treatment so as to yield the compound of formula (III).

5. A process for the preparation of the compound of formula (I), as claimed in claim 3, which alternatively further comprises an additional step of subjecting the compound of formula (V):

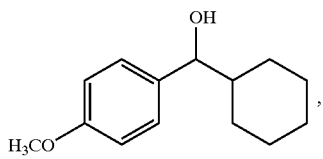
(V)

namely cyclohexyl-(4-methoxy-phenyl)-methanol, to oxidation so as to yield the compound of formula (III).

6. A process for the preparation of the compound of formula (I), as claimed in claim 5, which still further comprises the initial step of subjecting the compound of formula (VI):

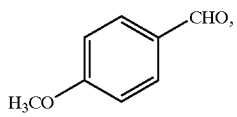
(VI)

namely 4-methoxybenzaldehyde, to treatment with a cyclohexyl magnesium halide, $C_6H_{11}$-Mg—X (where X=chlorine, bromine or iodine) so as to yield the compound of formula (V).

7. A process for the preparation of the compound of formula (I), as claimed in claim 5, which alternatively further comprises an initial step of treating the compound corresponding to formula (XI):

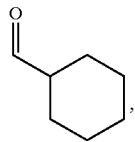
(XI)

namely cyclohexane-carbaldehyde, with anisyl magnesium halide or anisyl lithium, so as to yield the compound of formula (V).

8. A process for the preparation of the compound corresponding to formula (I) as claimed in claim 1, in which the compound corresponding to formula (VII):

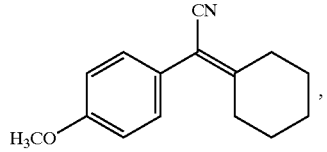
(VII)

namely cyclohexylidene-(4-methoxy-phenyl)-acetonitrile, is treated with an epoxidating agent to yield the desired compound of formula (I).

9. A process for the preparation of the compound corresponding to formula (I), as claimed in claim 8, which further comprises a previous step of preparing the compound of formula (VII), by treating the compound corresponding to formula (VIII):

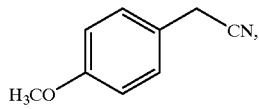
(VIII)

namely (4-methoxy-phenyl)-acetonitrile with cyclohexanone and a condensing agent, to secure the compound of formula (VII).

10. A process for the preparation of the compound corresponding to formula (I) as claimed in claim 1, in which the compound corresponding to formula (XII):

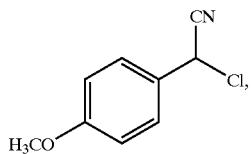
(XII)

namely chloro-(4-methoxy-phenyl)-acetonitrile, is subjected to Darzen's condensation treatment using cyclohexanone, in the presence of a base, to yield the desired compound of formula (I).

11. A process for the preparation of a compound corresponding to formula (IX):

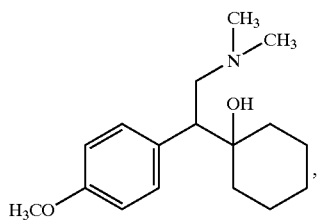
(IX)

namely ±1-[2-amino-1-(4-methoxy-phenyl)-ethyl] cyclohexanol, using the compound corresponding to formula (I) as claimed in claim 1 as a intermediate, which process comprises at least a first step of:
(a) hydrogenating a compound corresponding to formula (I) as claimed in claim 1, in the presence of a catalyst, so as to yield the compound corresponding ti formula (X):

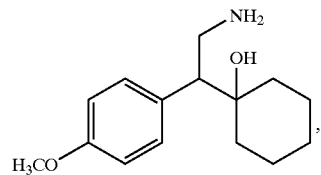
(X)

namely 1-[2-amino-1(4-methoxy-phenyl)-ethyl] cyclohexanol.

12. A process as claimed in claim 11, wherein the compound corresponding to formula (I) is reduced by treatment with ammonium formate and hydrogen in the presence of a catalyst selected from noble metal and supported noble metal catalysts, so as to yield the compound of formula (X).

13. A process as claimed in claim 11, wherein step (a) involves the production of an intermediate corresponding to formula (XIII):

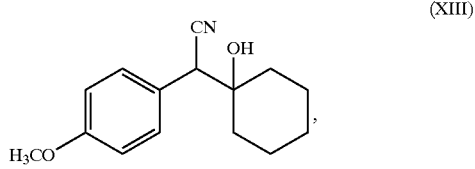

namely (1-hydroxy-cyclohexyl)-(4-methoxy-phenyl)-acetonitrile, which is subsequently reduced to the compound of formula (X).

14. A process as claimed in claim 13, wherein the compound of formula (XIII) is further reduced by treatment with a catalyst selected from Raney nickel, platinum dioxide, palladium, cobalt boride, nickel boride, or other suitable catalysts known from the literature, so as to yield the compound of formula (X).

15. A process as claimed in subsequent claim 2, wherein:
the cyanation agent is selected from sodium cyanide or potassium cyanide;
the reaction is performed in solution, the solvent being selected from methanol, ethanol, isopropyl alcohol, acetonitrile, dimethyl formamide, dimethyl sulphoxide, dimethyl acetamide, hexamethylene phosphoric triamide (HMPT), ethyl acetate or sulfolane; or benzene, toluene, cyclohexane dichloromethane, or chloroform in the presence of a phase transfer catalyst;
the ratio of solvent to (1-bromo-cyclohexyl)-(4-methoxy-phenyl)-methanone (II) is in the range of from 1:1 to 100:1;
the reaction is carried out at a temperature in the range of from −10 to 60° C.; and
the reaction is carried out for a time in the range of from 2 to 48 hours.

16. A process as claimed in claim 15 above, wherein:
the cyanation agent is sodium cyanide;
the solvent is methanol;
the ratio of solvent to the compound of formula (II) is substantially 25:1;
the reaction temperature is in the range of from 20 to 25° C.; and
the reaction time is in the range of from 6 to 8 hours.

17. A process as claimed in claim 3, wherein:
the α-keto-hydrogenating agent is a brominating agent selected from phenyl-trimethyl-ammonium perbromide, liquid bromine, N-bromo succinimide, 1,3 dibromo-5,5-dimethyl hydantoin, quaternary ammonium and phosphonium perbromides, N-chlorosuccinimide, or other known halogenating agents;
the reaction is carried out in a solvent selected from methanol, acetic acid, benzene, toluene, chloroform, carbon tetrachloride, tetrahydrofuran, acetonitrile, ethanol, dichloromethane, dioxane, t-butanol, or substituted benzenes; and
the ratio of solvent to ketone (III) is in the range of from 1:1 to 100:1.

18. A process as claimed in claim 17 above, wherein:
the α-keto-halogenating agent is phenyl trimethyl ammonium perbromide;
the ratio of solvent to ketone (III) is substantially 20:1; and
the reaction is carried out at a temperature of substantially 68° C., for a time of substantially 6 hours.

19. A process as claimed in claim 4, wherein:
the acylation treatment is carried out using cyclohexane carbonyl chloride, and a Friedel-Crafts reagent selected from aluminium trichloride, boron trifluoride or sodium aluminium chloride;
the reaction is carried out in a solvent selected from methoxy-benzene and halogenated or nitrated benzenes;
the ratio of solvent to cyclohexane-carbonyl chloride is in the range of from 5:1 to 50:1; and
the reaction is carried out at a temperature in the range of from −20 to 40° C.

20. A process as claimed in subsequent claim 5, wherein:
the oxidation is performed using an oxidising agent selected from chromic acid, alkali and alkaline earth metal chromates and dichromates, chromic anhydride, manganese dioxide, alkali and alkaline earth metal manganates, permanganates, nitric acid, alkali and alkaline earth metal persulphates, quaternary ammonium and phosphonium manganates and permanganates, chromates and other known oxidising agents.

21. A process as claimed in claim 20, wherein:
the oxidising agent is chromic acid; and
the oxidation is carried out at a temperature in the range of from 25 to 30° C., for a time of substantially 3 hours.

22. A process as claimed in claim 6, wherein:
the cyclohexyl magnesium halide is cyclohexyl magnesium bromide; and
the reaction is carried out at a temperature in the range of from 10 to 15° C. for a period of substantially one hour.

23. A process as claimed in claim 8, wherein:
the epoxidating agent is selected from m-chloroperbenzoic acid (m-CPBA), perbenzoic acid, peracetic acid, performic acid and other organic peracids, hydrogen peroxide, persulphuric acid, alkylhydroperoxides, and other known epoxidating agents;
the reaction is carried out in a solvent selected from dichloromethane, dichloroethane, carbon tetrachloride, chloroform, ethyl acetate and toluene;
the reaction is carried out at a temperature in the range of from 0° C. to the reflux temperature of the solvent; and
the reaction is carried out for a time in the range of from 1 to 48 hours.

24. A process as claimed in claim 23 above, wherein:
the epoxidating agent is m-chloroperbenzoic acid (m-CPBA);
the solvent is dichloromethane;
the reaction temperature is substantially 40° C.; and
the reaction time is in the range of from 6 to 8 hours.

25. A process as claimed in claim 9, wherein:
the condensing agent is selected from sodium methoxide, sodium ethoxide, potassium t-butoxide, quaternary ammonium hydroxide and other alkali and alkaline earth metal alkoxides, alkali and alkaline earth metal hydrides, or alkali and alkaline earth metal amides;
the reaction is carried out in a solvent selected from methanol, ethanol, t-butanol or other known solvents;
the reaction is carried out for a time in the range of from 1 to 24 hours; and
the reaction is carried out at a temperature in the range of from 10 to 60° C.

26. A process as claimed in claim 25 above, wherein:
the condensing agent is sodium methoxide;
the solvent is methanol;
the reaction time is in the range of from 3 to 6 hours; and
the reaction temperature is substantially 25° C.

27. A process as claimed in claim 11, which additionally comprises the further step of:
(b) treating the compound corresponding to formula (X) with formaldehyde and formic acid, to yield the compound of formula (IX).

28. A process as claimed in claim 11, wherein:
the catalyst in step (a) is selected from Raney nickel, platinum dioxide, platinum and palladium and nickel on different inert supports, aluminium hydride, lithium aluminium hydride, sodium borohydride or potassium borohydride, or lithium borohydride in the presence of Lewis acids such as quaternary ammonium borohydrides, neat or in the presence of a phase transfer catalyst;
the hydrogenation is carried out at a temperature in the range of from 0 to 100° C.; and
step (a) is carried out in a solvent selected from tetrahydrofuran (THF), dioxane, glyme, dialkylethers, polyethers or ethyl acetate.

29. A process as claimed in claim 28, wherein:
the catalyst in step (a) is Raney nickel, present in a ratio relative to the epoxy nitrile (I) in the range of from 5:1 to 1:5;
the hydrogenation is carried out at room temperature, and at a pressure in the range of from 500 to 1000 kPa; and
step (b) is performed at a temperature of substantially 100° C. for a time of substantially 6 hours.

30. A process as claimed in claim 29, wherein the ratio of Raney nickel to epoxy nitrile (I) is substantially 1:1.

31. A process as claimed in claim 13, wherein the compound corresponding to formula (I) is reduced by treatment with ammonium formate in the presence of a catalyst selected from noble metal and supported noble metal catalysts, so as to yield the compound of formula (XIII).

* * * * *

UNITED STATES PATENT AND TRADEMARK OFFICE
CERTIFICATE OF CORRECTION

PATENT NO.        : 6,756,502 B2                                     Page 1 of 1
APPLICATION NO.   : 10/119287
DATED             : June 29, 2004
INVENTOR(S)       : Dhiraj Mohansinh Rathod et al.

It is certified that error appears in the above-identified patent and that said Letters Patent is hereby corrected as shown below:

Title page, item (30) Foreign Priority Application Data, after "01303347" insert -- .7-2117--.
Title page, item (57) Abstract, Line 11, delete "x-keto-halogenation" and insert -- α-ketohalogenation -- therefor.
Column 16, Line 40, delete "±" and insert -- (±) -- therefor.
Column 16, Line 47, delete "ti" and insert -- to -- therefor.
Column 16, Line 58, delete "[2-amino-1(4" and insert -- [2-amino-1-(4 -- therefor.

Signed and Sealed this

Twenty-eighth Day of November, 2006

JON W. DUDAS
*Director of the United States Patent and Trademark Office*